United States Patent [19]

Ogata et al.

[11] Patent Number: 4,780,465
[45] Date of Patent: Oct. 25, 1988

[54] AQUEOUS SOLUTION CONTAINING A QUINOLONE CARBOXYLIC ACID

[75] Inventors: Kazumi Ogata, Toyonakshi; Hideo Terayama, Itamishi; Satoshi Takei, Amagasakishi, all of Japan

[73] Assignee: Hokuriku Pharmaceutical Co., Ltd., Katsuyajashi, Japan

[21] Appl. No.: 52,576

[22] Filed: May 20, 1987

[30] Foreign Application Priority Data

Jan. 14, 1987 [JP] Japan ................................ 62-006727

[51] Int. Cl.$^4$ ..................... A61K 31/50; A61K 31/495
[52] U.S. Cl. ................................................... 514/254
[58] Field of Search ........................................ 514/254

[56] References Cited

U.S. PATENT DOCUMENTS

| | | | |
|---|---|---|---|
| 4,017,622 | 4/1977 | Minami et al. | 514/254 |
| 4,292,317 | 9/1981 | Pesson | 514/254 |
| 4,528,287 | 7/1985 | Itoh et al. | 514/254 |
| 4,551,456 | 11/1985 | Katz | 514/254 |
| 4,670,440 | 2/1987 | Szüts et al. | 514/254 |

FOREIGN PATENT DOCUMENTS 0187315 7/1986 European Pat. Off. .

*Primary Examiner*—Stanley J. Friedman
*Attorney, Agent, or Firm*—Gordon W. Hueschen

[57] ABSTRACT

A stable isotonic aqueous solution of the compound 1-ethyl-6,8-difluoro-1,4-dihydro-7-(3-methyl-1-piperazinyl)-4-oxoquinoline-3-carboxylic acid, or a pharmaceutically-acceptable salt thereof, having a pH of 3 to 6.5 and isotonized with a polyalcohol or boric acid is disclosed.

7 Claims, No Drawings

AQUEOUS SOLUTION CONTAINING A QUINOLONE CARBOXYLIC ACID

The present invention relates to a stable isotonic aqueous solution of a specific quinolone carboxylic acid biocide or a salt thereof.

During the last few years, remarkable progress has been made in the area of synthetic antimicrobial agents, especially in the form of quinolone carboxylic acids. The quinolone carboxylic acid derivatives of this invention are disclosed in U.S. Pat. No. 4,528,287, issued July 9, 1985, and in Japan Kokai No. 60-64979. For the use of these compounds for injectable, ophthalmic, or intranasal solutions, ear drops, or other aqueous pharmaceutical solutions, the compounds must be sufficiently soluble in water and their aqueous solution must be isotonic and stable to light and heat. Microbiocidal solutions containing the quinolone carboxylic acid derivatives of the invention are described in Japan Kokai No. 61-180771. In this literature, their solution was adjusted basically, that is, to a pH of 8 to 11, to obtain stability. But, generally speaking, aqueous formulations are preferred to be at neutral or weakly-acidic pH conditions. For the preparation of injectable, ophthalmic, or other pharmaceutical solutions, it is likewise preferred to employ neutral or slightly-acidic conditions so as to isotonize the osmotic pressure and thus to avoid irritation and tissue injury. However, when it is attempted to isotonize the compound of this invention with an isotonizing agent selected from sodium chloride, potassium chloride, or other usual and analogous compounds, the maximum concentration of this compound becomes less than that concentration which exhibits pharmaceutical activity and a desirable aqueous formulation cannot be produced. Now, in accordance with the present invention, a stable aqueous and isotonic solution is obtained in the following manner: To the compound 1-ethyl-6,8-difluoro-1,4-dihydro-7-(3-methyl-1-piperazinyl)-4-oxoquinoline-3-carboxylic acid, represented by the following formula, designated compound (I),

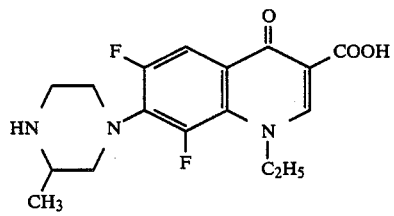

or a pharmaceutically-acceptable salt thereof, is added (in any order) water and a polyalcohol or boric acid to isotonize the solution, and the solution is adjusted to a pH of 3 to 6.5.

By our research to produce non-irritating, stable, and isotonic aqueous solutions containing the compound (I) or a salt thereof, the desired aqueous isotonic solution was found to be attainable by including a polyalcohol or boric acid to isotonize the solution and then adjusting to a pH value of 3 to 6.5. Thus, under such conditions according to the invention, the compound (I) immediately exhibits increased solubility in water in the region below pH of about 6.5 or above pH of about 9, for example, the solubility becoming higher than the necessary or appropriate concentration (about 0.3 w/v%) for ophthalmic solutions and ear drops. However, in contrast, the compound exhibits a diminished solubility in water at the desired pH of 3 to 6.5 when sodium chloride, potassium chloride, or analogous usual isotonizing agents are attempted to be employed. As a result of further research however, it was found that the use of a polyalcohol or boric acid as an isotonic agent leads to a stable and isotonic aqueous solution possessing a suitable solubility above the necessary and appropriate concentration and at the correct pH level.

The aqueous solution of this invention is useful as an injectable solution, for ear drops, as an intranasal or opthalmic solution, or the like, in each case containing the compound (I), or a salt thereof, having a wide antibacterial spectrum for Gram positive and Gram negative microorganisms.

The compound (I) may be used as the free basic compound or as a salt thereof with an inorganic base (e.g., NaOH, KOH, etc.), with an organic base (e.g., mono-, di-, trialkyl-amine, etc.), with an inorganic acid (e.g., HCl, $HNO_3$, etc.), with an organic acid (e.g., acetic acid, citric acid, etc.). Glycerine, mannitol, glucose, xylitol, xylose, sorbitol, and propylene glycol are illustrative of suitable polyalcohols. The concentration of the compound (I) or salt thereof is about 0.01% to about 10%, preferably about 0.3% to about 5% w/v. Sufficient polyalcohol or boric acid, or both, are added to isotonize, for example, boric acid is used in an amount of about 1.9%, glycerine in an amount of about 2.6%, mannitol in an amount of about 5.1%, and glucose in an amount of about 5.1%. Boric acid is preferably used only for topical preparations because it has greater than optimum toxicity. The pH of the aqueous solution is between 3 and 6.5, with a range of 4 to 6.5 being preferred. Adjustment of pH is effected by any common procedure, for example, by the employment of an organic or inorganic acid or base.

So far as compatible with the objects of the invention, excipients employed for usual aqueous solutions, e.g., buffers to adjust the pH (phosphate buffer, borate buffer, citrate buffer, acetate buffer, etc.), preservatives (benzalkonium chloride, p-hydroxybenzoate, benzyl alcohol, p-chloromethoxyphenols, chlorocresols, phenethyl alcohol, sorbic acid or its salts, methylosal, chlorobutanols, etc.), chelating agents (sodium edetate, sodium citrate, condensed sodium phosphate, etc.) may be added to, and/or present in conventional quantities in, the aqueous solution of this invention. These substances may be premixed in the aqueous solution, mixed with polyalcohol or boric acid, or added subsequently.

According to the circumstances, an aqueous solution may first be prepared with the polyalcohol or boric acid and excipients and the compound (I) or its salt then added. In either case, one can select a suitable procedure whereby at least one of the polyalcohol and boric acid is introduced into the acidic solution of the compound (I) or a salt thereof. Other medicinal ingredients besides the compound (I) or a salt thereof can also be added, if desired.

The following examples illustrate the formulations of the present invention, their preparation, and their utility, but are not to be considered limitative of the invention.

EXAMPLE A

The Effect of Isotonic Agents Upon the Solubility of the Compound (I).HCl

To a mixture of water and isotonic agents was added the Compound (I).HCl to make a 2% w/v solution, following adjustment to pH 5 with NaOH solution. The thus-obtained solution was shaken in a thermostat for 24 hours. After filtration with 0.45 μm filter, the content of the compound (I).HCl in the solution was measured by HPLC method. The pH value after filtration was 5. The results are illustrated in Table I.

TABLE I

| Isotonic agent (concentration) | | Solubility of compound (I).HCl |
| --- | --- | --- |
| None | | 1.3% |
| NaCl | (0.9%) | 0.16% |
| KCl | (1.2%) | 0.17% |
| Boric acid | (1.9%) | 1.3% |
| Glycerine | (2.6%) | 1.2% |
| Mannitol | (5.1%) | 1.3% |
| Glucose | (5.1%) | 1.3% |

The usual agents NaCl and KCl reduces the solubility, but glycerine, mannitol, and glucose do not reduce the solubility.

EXAMPLE B

Stability Test

The following formulations were packed in a polypropylene container and stored under the described condition illustrated by the Table II. Samplings were taken at the time indicated in Table II, and the appearance, pH, and percentage change in concentration of the compound (I).HCl were determined. The concentration of the compound (I).HCl was measured by high speed liquid chromatography.

| Formulation | |
| --- | --- |
| Compound (I).HCl | 0.3 g |
| Conc. glycerine | 2.4 g |
| EDTA.2Na | 0.01 g |
| Benzalkonium chloride | 0.002 g |
| NaOH | adequate amount |
| sterilized purified water pH 6 | q.s to 100 ml |

TABLE II

| | | Remaining proportion | pH (%) | Appearance |
| --- | --- | --- | --- | --- |
| Start | | 100.0 | 6.0 | colorless and transparent |
| Room temperature | 1 month | 100.0 | 6.0 | colorless and transparent |
| | 2 month | 100.0 | 6.0 | colorless and transparent |
| | 3 month | 99.6 | 6.0 | colorless and transparent |
| 40° C. | 1 month | 100.0 | 6.0 | colorless and transparent |
| | 2 month | 100.0 | 6.0 | colorless and transparent |
| | 3 month | 99.4 | 6.0 | colorless and transparent |
| 60° C. | 1 month | 99.9 | 6.0 | colorless and transparent |
| Indoor dispersed light | 1 month | 98.7 | 6.0 | colorless and transparent |

As indicated in Table II, no significant changes in coloring, precipitation, pH, or decline in content of active ingredient were observed.

The salts of the compound (I) with an organic or inorganic acid other than the hydrochloride salt show the same effects as indicated in Table I and II.

EXAMPLE 1

| Opthalmic solution, ear drops, and intranasal solution: | |
| --- | --- |
| Compound (I).HCl | 0.3 g |
| Conc. glycerine | 2.4 g |
| EDTA.2Na | 0.01 g |
| Benzalkonium chloride | 0.002 g |
| NaOH | adequate amount |
| Sterilized purified water pH 6 | q.s. to 100 ml |

EXAMPLE 2

| Opthalmic solution: | |
| --- | --- |
| Compound (I).HCl | 0.3 g |
| Boric acid | 1.8 g |
| Sodium edetate | 0.01 g |
| Methyl paraben | 0.02 g |
| NaOH | adequate amount |
| Sterilized purified water pH 6 | q.s. to 100 ml |

EXAMPLE 3

| Solution For Injection: | |
| --- | --- |
| Compound (I) | 0.3 g |
| Mannitol | 4.8 g |
| NaOH | adequate amount |
| Sterilized purified water pH 6 | q.s. to 100 ml |

In conclusion, from the foregoing, it is apparent that the present invention provides a novel and useful microbiocidally-effective isotonic aqueous solution of 1-ethyl-6,8-difluoro-1,4-dihydro-7-(3-methyl-1-piperazinyl)-4-oxoquinoline-3-carboxylic acid or a salt thereof, having a broad sphere of utility, and having the foregoing enumerated characteristics and advantages.

It is to be understood that the invention is not to be limited to the exact details of operation or to the exact compounds, compositions, methods, procedures, or embodiments shown and described, as modifications and equivalents will be apparent to one skilled in the art, and the invention is therefore to be limited only by the full scope which can be legally accorded to the appended claims.

What is claimed is:

1. A stable isotonic aqueous solution consisting essentially of an effective microbiocidal amount of the compound, 1-ethyl-6,8-difluoro-1,4-dihydro-7-(3-methyl-1-piperazinyl)-4-oxoquinoline-3-carboxylic acid or a pharmaceutically-acceptable salt as essential active microbiocidal ingredient thereof, and an isotonizing amount of a compound selected from the group consisting of a polyalcohol, selected from the group consisting of glycerine, mannitol, glucose, xylitol, xylose, sorbitol, and propylene glycol, and boric acid as isotonizing agent for the solution, the solution being adjusted to a pH of about 3 to 6.5.

2. Solution of claim 1 wherein the amount of the essential active microbiocidal ingredient is 0.01 to 10 percent weight per volume.

3. Solution of claim 2 wherein the amount of the essential active microbiocidal ingredient is 0.3 to about 5 percent weight per volume.

4. Solution of claim 3 wherein the pH is 4–6.5.

5. Solution of claim 4 wherein the essential active microbiocidal ingredient is 1-ethyl-6,8-difluoro-1,4-dihydro-7-(3-methyl-1-piperazinyl)-4-oxoquinoline-3-carboxylic acid hydrochloride.

6. Solution of claim 5, wherein the isotonizing compound is selected from the group consisting of glycerine, mannitol, and glucose.

7. Solution of claim 5, wherein the isotonizing agent is glycerine.

* * * * *

UNITED STATES PATENT AND TRADEMARK OFFICE
CERTIFICATE OF CORRECTION

PATENT NO. : 4,780,465

DATED : October 25, 1988

INVENTOR(S) : Kazumi Ogata, Hideo Terayama and Satoshi Takei

It is certified that error appears in the above-identified patent and that said Letters Patent is hereby corrected as shown below:

Title Page [56] References Cited, U.S. PATENT DOCUMENTS, last line; "2/1987" should read -- 6/1987 --

Col. 3, line 18; "reduces" should read -- reduce --
Col. 3, line 28; "time" should read -- times --
Col. 4, line 67; "is 0.3" should read -- is about 0.3 --

Signed and Sealed this

Twenty-first Day of March, 1989

Attest:

DONALD J. QUIGG

*Attesting Officer*   *Commissioner of Patents and Trademarks*